(12) United States Patent
Hellenkamp

(10) Patent No.: US 6,610,076 B2
(45) Date of Patent: *Aug. 26, 2003

(54) POSITIONING ASSEMBLY FOR RETAINING AND POSITIONING A CORNEA

(76) Inventor: Johann F. Hellenkamp, 10060 SW. 89th Ct., Miami, FL (US) 33176

( * ) Notice: Subject to any disclaimer, the term of this patent is extended or adjusted under 35 U.S.C. 154(b) by 0 days.

This patent is subject to a terminal disclaimer.

(21) Appl. No.: 09/902,459

(22) Filed: Jul. 10, 2001

(65) Prior Publication Data

US 2002/0082628 A1 Jun. 27, 2002

Related U.S. Application Data

(63) Continuation of application No. 09/404,775, filed on Sep. 24, 1999, now Pat. No. 6,258,110, which is a continuation-in-part of application No. 08/840,430, filed on Apr. 29, 1997, now Pat. No. 6,296,649, which is a continuation of application No. 08/598,180, filed on Feb. 7, 1996, now Pat. No. 5,624,456.

(51) Int. Cl.7 .............................................. A61F 09/007
(52) U.S. Cl. ........................................................ 606/166
(58) Field of Search .......................... 606/166, 5, 161, 606/167, 170, 180, 172

(56) References Cited

U.S. PATENT DOCUMENTS 5,586,980 A * 12/1996 Kremer et al. ................. 606/4
5,624,456 A * 4/1997 Hellenkamp ................ 606/166
6,007,553 A * 12/1999 Hellenkamp et al. ....... 606/166

OTHER PUBLICATIONS

"Lamellar Refractive Kertoplasy", Bores Eye Institute, Chapter 4, pp. 1–9, 1988.*

* cited by examiner

Primary Examiner—Michael H. Thaler
(74) Attorney, Agent, or Firm—Malloy & Malloy, P.A.

(57) ABSTRACT

A positioning assembly for retaining, positioning and at least partially exposing a cornea of an eye during a surgical procedure. The positioning assembly includes a positioning segment having a retention plate with an aperture to receive and expose the cornea, and a flange member disposed about the aperture and structured to engage the eye. The positioning assembly further includes a suctioning assembly having a vacuum port extending vertically from the positioning segment and angled outwardly away from a guide track integrally disposed on the retention plate to define an arcuate cutting path for a microkeratome cutting head assembly. A pivot assembly including at least a post member is further provided which operably interconnects the cutting head assembly and the post member. A cut origination control is provided at the post member to define an origination point.

3 Claims, 3 Drawing Sheets

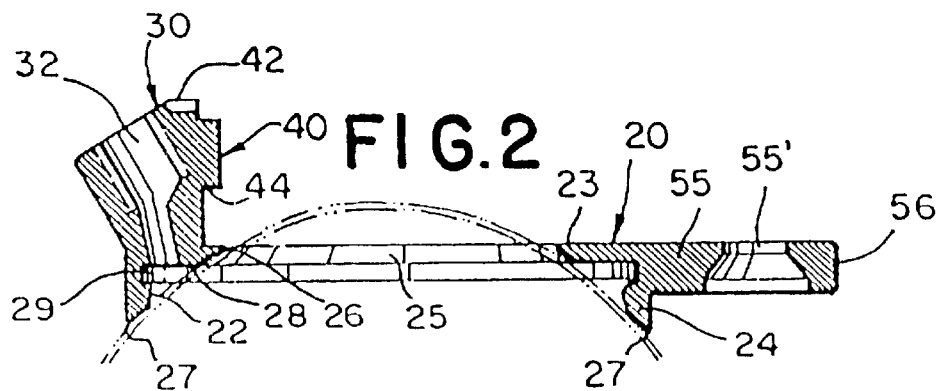
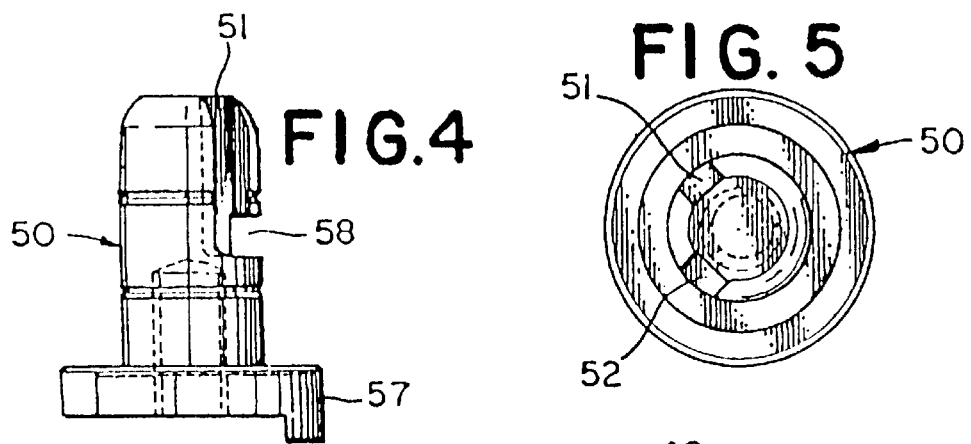
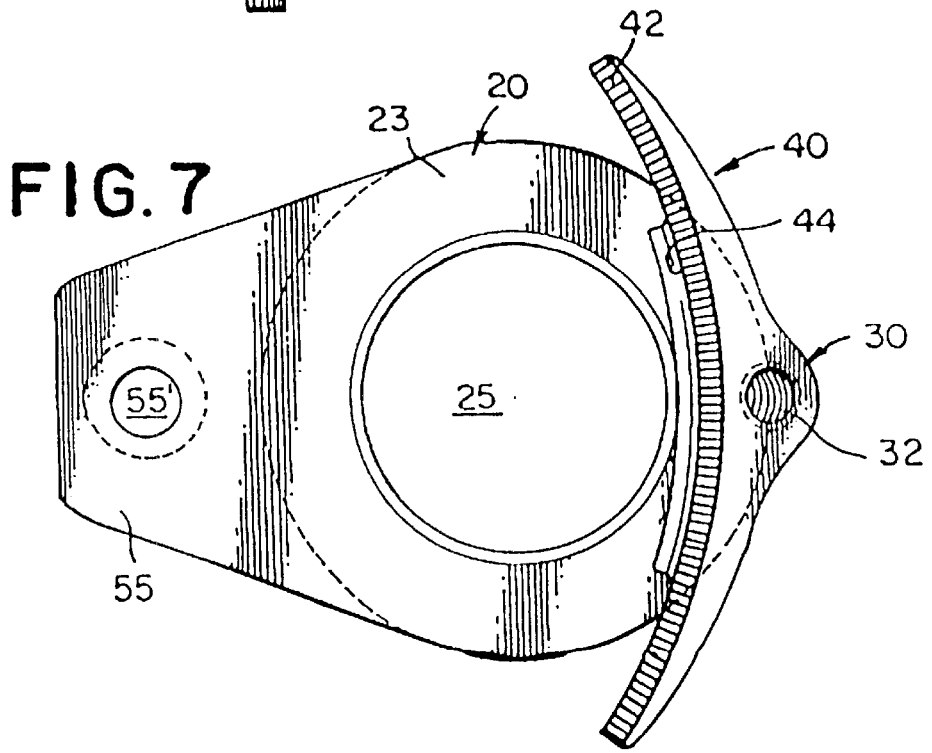

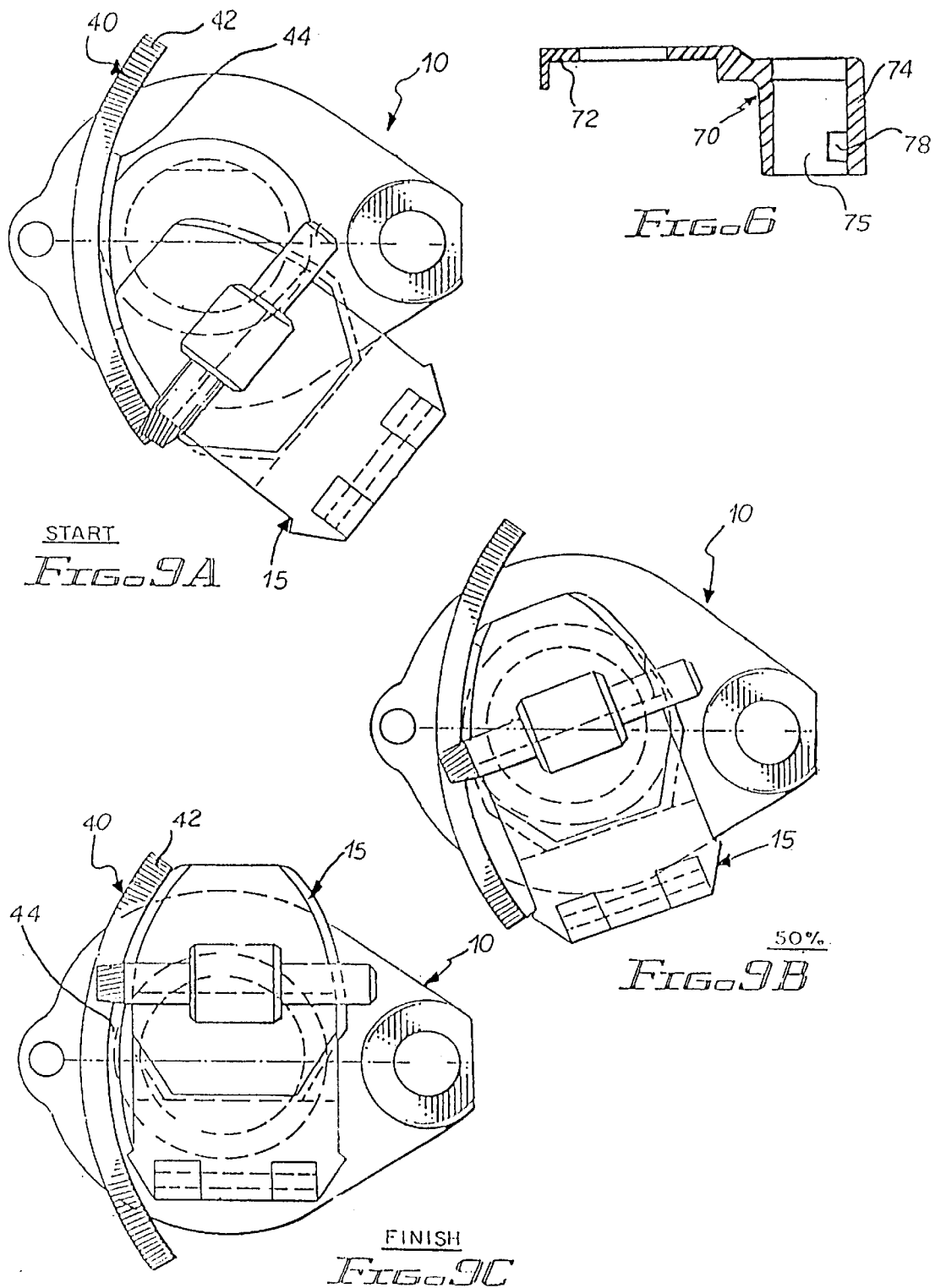

POSITIONING ASSEMBLY FOR RETAINING AND POSITIONING A CORNEA

This is a continuation application based on U.S. patent application having Ser. No. 09/404,775, filed on Sep. 24, 1999, now U.S. Pat. No. 6,258,110 which is a continuation-in-part patent application based on U.S. patent application having Ser. No. 08/840,430, filed on Apr. 29, 1997, now U.S. Pat. No. 6,296,649 which is a continuation patent application filed on Feb. 7, 1996 and having Ser. No. 08/598,180, which since issued as U.S. Pat. No. 5,624,456 on Apr. 29, 1997, the contents of all of which are hereby incorporated herein by reference.

BACKGROUND OF THE INVENTION

1. Field of the Invention

The present invention relates generally to a medical apparatus used during the performance of eye surgery, and in particular, is directed towards an improved suction ring, also termed a positioning assembly, for retaining, positioning and exposing a patient's eye for cutting of the cornea during a surgical procedure, such as to correct for refractive error. More specifically, the present invention is directed to an easily assembled and safe to use positioning assembly which minimizes the potential for improper cutting of the eyelid and/or eye, and further, which is capable of achieving and maintaining effective attachment on an eye, even one having a latitudinally narrowed ocular access, such as may be encountered in certain individuals, most notably, but not exclusively, children and persons of Asian descent.

2. Description of the Related Art

The eye works on a principle very similar to that of a camera wherein the iris, or colored portion of the eye about the pupil, functions like a shutter to regulate the amount of light admitted to the interior of the eye. The cornea or clear window of the eye, and the lens, which is located behind the pupil, serve to focus the light rays from an object being viewed onto the retina at the back of the eye. The retina then transmits the image of the object viewed to the brain via the optic nerve. Normally, these light rays will be focused exactly on the retina, which permits the distant object to be seen distinctly and clearly. Deviations from the normal shape of the corneal surface however, produce errors of refraction in the visual process so that the eye becomes unable to focus the image of the distant object on the retina, with the result that one sees a blurred image.

Many years ago, such refractive errors could only be treated with eyeglasses or contact lens, both of which have well known disadvantages for the user. Since then, however, surgical operations have been developed to change the refractive condition of the eye. Several methods and special instruments have been designed for performing this kind of surgery, which are primarily directed to reshape the cornea. It will be appreciated that the goal of corneal reshaping is to modify the curvature of the cornea, i.e., either to flatten or increase its curvature depending on the patient's condition, so that light rays passing through the cornea will thereafter be refracted to focus or converge directly onto the retina, thereby permitting Gus the patient to view a distant object clearly.

One such surgical operation is keratomileusis, which requires a precise reshaping of the cornea by cutting and separating a thin layer of corneal tissue, termed the corneal cap, by lathing that tissue and then, by suturing the reshaped corneal tissue back into place on the eye. Keratomileusis is viewed, however, as having several drawbacks, and consequently, has been abandoned in recent years. Automated Lamellar Keratectomy (ALK) is another surgical technique which developed as an outgrowth of keratomileusis. In an ALK procedure, the eye is typically first numbed by a drop of anesthetic, and then, a device having a ring shaped configuration is placed on the eye to carefully position the cornea (termed "centration" in the art) for being cut by a very fine microsurgical instrument known as a microkeratome. The microkeratome is generally a blade carrying device that must be manually pushed or mechanically driven in a cutting path across the ring shaped device to cut into the cornea. Under an ALK procedure to treat nearsightedness, the microkeratome is typically first used to cut and lift a thin layer of the cornea, instead of severing it, and second, to carry out a reshaping of the cornea by way of a second pass of the microkeratome over the cornea with the cutting element adjusted to pass therethrough at a desired and pre-determined corrective depth. Thereupon the thin, raised layer of corneal tissue is put back in place over the cornea for healing.

There have been other significant developments in this field of art, however. For example, a procedure known as Laser Intrastromal Keratomileusis (LASIK), wherein a laser is utilized to re-shape and/or contour the cornea, is becoming increasingly accepted as both a safe, painless and rapidly effective procedure for correcting vision problems such as, but not limited to, nearsightedness, farsightedness and astigmatism, both regular and irregular. The LASIK procedure is currently considered optimal because it allows sculpting of the cornea without damaging adjacent tissues, and further, because with the aid of computers, the laser can be programmed by a surgeon to more precisely control the amount of tissue removed, and significantly, to permit more options for the reshaping of the cornea. Under LASIK procedures, the eye is still typically positioned within a ring shaped device and a microkeratome cutting head assembly is typically also used as a preliminary step to cut and raise a thin layer of corneal tissue in order to expose underlying portions of the eye for treatment with the laser. The cutting of a thin layer of corneal tissue is commonly known as a keratectomy, and in the most common case, a "corneal flap" will be cut, which leaves a hinged portion of tissue attached to the cornea, although there are special cases where a "free cap" is cut wherein the raised layer of corneal tissue is left detached from the eye.

Turning more specifically to how the eye is maintained in the desired position for a LASIK procedure, the ring shaped device referred to above is commonly used and is attached to the eyeball temporarily by way of a suctioning force or vacuum. As such, such devices are often referred to as suction rings, and a typical suction ring includes an annular, hollow ring that defines a central aperture, which allows the cornea to be exposed therethrough, and an open bottom side having a standard dimension and which is structured to engage the surface of the eye around the cornea. The suction ring is typically in communication with a hollow suction tube, which is in fluid flow communication with the open bottom side of the ring. A vacuum is commonly applied to such suction rings, via the suction tube, with a relative vacuum of typically between 20" Hg and 28" Hg, being applied, which draws the suction ring down upon the globe of the eye under the influence of external atmospheric pressure. As such, the suction ring attaches to the surface of the eyeball surrounding the cornea, with the suction force being applied and holding the ring in a reasonably secure fashion to the eyeball throughout the LASIK procedure. As a result, the suction ring has become a conventional device in ophthalmic practice, and it should be noted, is designed to be re-usable so as to accommodate a large number of patients over the course of its useful life.

While the use of such suction rings have become quite common in the art, there have been some drawbacks associated with them. For example, the configuration and size of known suction rings do not readily permit them to be comfortably and/or properly positioned within the ocular recess of many persons. More specifically, it has been determined that some individuals, and especially children and persons of Asian decent, tend to exhibit certain physical characteristics which result in there being a somewhat constricted area available for placement of the suction ring. For example, such individuals may either have a more narrow ocular recess and/or may not be able to open their eyes as wide as some other persons, especially in the latitudinal and/or up and down direction. This restricted access can often lead to difficulties for the practitioner performing a surgical procedure such as LASIK on the eye, as an insufficient surface area for proper securement of a traditional suction ring exists.

As a result, it would be highly beneficial to provide a microkeratome assembly, and in particular an improved suction ring for use with such an assembly, which is especially well suited for use in the eyes of all patients, including those having latitudinally smaller ocular accesses. Any such improved suction ring developed, however, should be able to be effectively and comfortably secured to the exposed portions of the patient's eye, while still exposing and presenting a sufficient depth and/or diameter of the cornea for cutting by the microkeratome cutting head assembly. Furthermore, if any such improved suction ring were developed, it would be very it beneficial if it were structured for effective use with a cutting head assembly of the type configured to cut along an arcuate path, such as that disclosed in U.S. Pat. No. 5,624,456 and considered by many to perform a keratectomy with optimal results, without interfering with the cutting process and/or diminishing its accuracy, despite there being a more confined area or ocular recess.

It is also noted that conventional suction rings can be difficult to manufacture and/or assemble, particularly given the degree of precision which is necessary for safe and effective use during opthamological procedures. If a suction ring were developed which is suitable for a smaller ocular recess, which commonly found on children and persons of Asian descent, these issues would also have to be addressed satisfactorily. Thus, it would be beneficial to provide an improved suction ring or positioning assembly which integrates all of the necessary components into an efficient, streamlined, and compact configuration, which is readily capable of being manufactured accurately and precisely, and which still allows for the safe and precise utilization of a microkeratome assembly. Lastly, it would also be beneficial if any improved suction ring were developed which could reasonably ensure that during a keratectomy, the microkeratome cutting head assembly will initiate cutting of the cornea at a uniform and rather precise position relative to the eyelid and/or cornea so as to avoid the possibility that an improper cut will occur. More in particular, it would be beneficial to provide an improved suction ring or positioning assembly that does not allow the cutting of an incision to begin unless the cutting head assembly is properly positioned.

SUMMARY OF THE INVENTION

The present invention is structured to address these and other needs which remain in the art and is directed towards an improved suction ring, and more specifically, a positioning assembly for retaining and positioning the cornea of patient's eye for the performance of a surgical procedure thereon. The positioning assembly of the present invention is, in at least one embodiment, especially suited for use on patients exhibiting a latitudinally narrowed ocular recess or ocular access, meaning that dimension which corresponds to the direction of blinking, as is commonly found on children and individuals of Asian descent. Also, while the present invention has application to the eye of any patient, it is expected that it will typically be used on the human eye.

More in particular, the present invention is directed towards a positioning assembly which at least partially exposes, positions and retains an eye during a surgical procedure. The positioning assembly is, therefore, preferably incorporated as part of a microkeratome assembly, and as a result, may be utilized in conjunction with a microkeratome cutting head assembly that is configured to form an incision in and/or cut across the eye, whether that results in the creation of a corneal flap or not. The positioning assembly includes a positioning segment which is structured to retain and position the eye during the surgical procedure such that the cornea is maintained in a properly exposed position throughout. As such, the positioning segment includes a retention plate. The retention plate preferably includes a generally planar configuration, and has an aperture defined therein. The aperture, which in the preferred embodiment is generally centrally disposed on or within the retention plate, is structured to receive and expose the cornea of the eye therein, so as to generally define the area to be cut.

The position segment also includes a flange member. The flange member depends generally downward from the retention plate and is disposed in preferably enclosing relation about the aperture. As such, the flange member is structured to engage the eye at least substantially along a bottom edge thereof. Accordingly, a vacuum chamber is generally defined between the aperture, bottom edge of the flange member, and the surface of the eye extending therebetween. The flange member of the present invention is also preferably disposed a relatively close, spaced apart distance from the aperture of the positioning segment, at least generally along a latitudinal radius thereof. As a result, in circumstances wherein the patient has a latitudinally narrowed ocular access, not as much of the surface of the eye need be exposed by the ocular access in order to achieve effective contact between the positioning segment and the eye, and in order to effectively expose a sufficient quantity of the cornea within the aperture.

The positioning assembly of the present invention may further include, at least in part, a suctioning assembly. In particular, a suctioning assembly is preferably operatively associated with the positioning segment, preferably at the vacuum chamber, thereby at least temporarily attaching the positioning segment to the eye. Specifically, the suctioning assembly includes a vacuum port connected in fluid flow communication between the vacuum chamber and an exterior source of vacuum. As a result, a suction force is applied at the vacuum chamber, and effective securement of the positioning assembly to the eye is achieved. Preferably, however, the vacuum port, unlike traditional, perpendicularly-oriented vacuum ports, is at least partially angled outwardly away from the vertical axis of the aperture, thereby providing effective clearance for movement of the microkeratome cutting head assembly, as will be described subsequently herein.

In the more preferred embodiments of the present invention, the positioning assembly of the present invention includes a guide track. The guide track is preferably integrally formed by with the positioning segment, and further, defines a preferably arcuate cutting path, which guides the microkeratome cutting head assembly at least partially across the aperture defined in the retention plate. The guide track preferably extends latitudinally beyond the retention plate of the positioning segment and is preferably disposed in close proximity to the vacuum port. As such, the generally outward, angled nature of the vacuum port away from the guide track ensures that a suction tube or like structure coupled to the vacuum port will not interfere with the movement of the cutting head assembly in operative association with the guide track.

Additionally, the positioning assembly preferably includes a pivot assembly and associated coupling member. Specifically, the pivot assembly defines a pivot axis for the cutting head assembly, which as indicated preferably moves arcuately across the aperture as defined at least by the guide track and also preferably by the pivot assembly. Preferably, a post member is included in the pivot assembly to define the pivot axis about which the cutting head assembly rotates, the coupling member pivotally interconnecting the post member with the cutting head assembly at least for this purpose. The pivot assembly, however, also further comprises a cut origination control. The cut origination control is structured to define at least one origination point for the commencement of operative pivotal movement of the coupling member, and accordingly the cutting head assembly, across the positioning segment. As a result, a practitioner is ensured that the cutting head assembly engages the eye and begins the formation of the incision only at a proper point, such as at the edge of the aperture, and generally cannot be inadvertently positioned to form an incision commencing at an intermediary point of the exposed cornea.

These and other features of the present invention are described in further detail in the following detailed description and associated drawings.

BRIEF DESCRIPTION OF THE DRAWINGS

For a fuller understanding of the nature of the present invention, reference should be had to the following detailed description taken in connection with the accompanying drawings in which:

FIG. 2 is a cross section view of the positioning assembly of the present invention;

FIG. 4 is an isolated side view of the post member of the pivot assembly of the present invention;

FIG. 5 is a top plan view of the post member;

FIG. 6 is a cross-section of the coupling assembly;

FIG. 7 is a top plan view of the positioning assembly of the present invention without the post member and coupling assembly coupled thereto;

FIGS. 9A–9C are a series of sequential illustrations demonstrating a normal cutting path for a microkeratome assembly with which the positioning assembly of the present invention is preferably associated.

Like reference numerals refer to like parts throughout the several views of the drawings.

DETAILED DESCRIPTION OF THE PREFERRED EMBODIMENT

Figure 1:
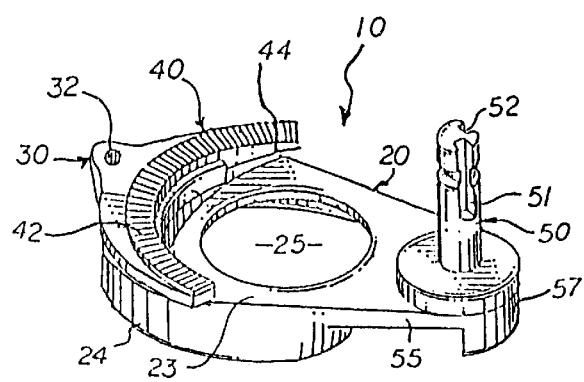
FIG. 1 is a perspective view of the positioning assembly of the present invention.

Illustrated throughout the drawings, the present invention is directed generally towards a positioning assembly for improved retaining and positioning of a patient's eye, and preferably the cornea of the patient's eye which is to be cut during a surgical operation, and is generally indicated by reference numeral 10. More specifically, the present invention is directed towards a more compact, precision assemblable and manufacturable, safety enhancing and stable positioning assembly 10 that can be used not only on the average patient, but which MS can also be used effectively on a patient having a latitudinally reduced ocular access wherein the eye is contained. In particular, the ocular access is generally defined as the eye socket and associated eye lid, all of which limit and/or otherwise restrict the amount of a patient's eyeball that can be exposed, such as for securing to a positioning assembly. In some cases, and most prevalently with children and patient's having characteristic, Asian facial features, the ocular access exhibits a smaller than normal latitudinal dimension. (For purposes of this description, a latitudinal dimension is defined as an up and down dimension relative to the patient's face, up being towards the patient's eyebrow and down being towards the patient's chin.) As a result, a conventional positioning assembly is generally not able to sufficiently engage the latitudinal sides of the eyeball. Naturally, such a restriction results in improper centration, and/or less of the cornea being exposed for cutting. As will be described, the present invention provides a more compact configuration, which is beneficial not only in the case of a latitudinally reduced ocular access, but which is generally beneficial when performing surgery on the eye for a variety of reasons including ease and precision of assembly, safety, and stability during cutting.

The positioning assembly 10 of the present invention is preferably directed for use with a microkeratome assembly such as, but not necessarily like the one described in U.S. Pat. No. 5,642,456, and incorporated herein by reference. As illustrated in FIGS. 1, 2 and 7, the positioning assembly 10 comprises a positioning segment 20, also known as an eye positioning ring. The positioning segment 20 preferably includes an enclosed ring configuration, so as to maximize its engagement with the eye, and is used to centrate the eye, that is, to retain, position and properly present the cornea of a patient's eyeball in a precise and aligned manner for surgery. Thus, the positioning segment 20 has a main body which includes and defines a preferably enclosed aperture 25 therein. The aperture 25 is sized to receive and permit the cornea C, of the eye to pass therethrough so as to expose the cornea C, and a pre-determined depth thereof, for cutting during surgery. Typically, the cornea C will be cut during surgery when a microkeratome cutting head assembly 15, also preferably part of the microkeratome assembly, is moved over the face of the positioning segment 20 and thus, over the exposed cornea C, which as is clear from the drawings, protrudes through the aperture 25. The aperture 25 itself is preferably sized to expose a sufficient amount of the cornea so that a diameter of generally about 7.5 to 10 millimeters may be cut. The positioning segment 20 is preferably formed of a rigid material and preferably, a metallic material. Ideally, however, the positioning segment 20 will be made of a high grade stainless steel, which enhances precision engagement with the eyeball, can go be formed to have a smooth, safe and glare-retardant surface finish, and which provides for ease of sterilization. Along these lines, although the present positioning assembly may be made disposable, out of a variety of materials, and/or molded of plastic or metal, in the illustrated embodiment, the positioning assembly 10 is preferably machined so as to achieve the degree of precision and quality generally desired.

As illustrated in the figures, the main body of the positioning segment 20 is preferably defined by a generally circular shape about the aperture 25, although it will be appreciated that it could be formed to have another shape, such as a square, rectangular, hexagonal or other shape about the aperture 25, and still function for the intended purpose. Moreover, the entire positioning assembly 10 is preferably configured in a generally tear drop type shape. In the preferred embodiment, the main body of the positioning segment 20 comprises a retention plate 23, which includes the aperture 25 defined therein, and preferably a flange member 24 extending generally downwardly from the retention plate 23 and defining a generally open bottom side to the main body. Ideally, the flange member 24 is disposed in spaced apart, generally surrounding relation to the aperture 25 defined in the retention plate 23. Also in the preferred embodiment, the flange member 24 of the positioning segment 20 preferably includes a lower edge 27 which is structured and disposed to engage the portion of the eye about the cornea in a fluid impervious manner. Similarly, the retention plate 23 may also be said to include an interior rim 26 disposed in surrounding, defining relation about the aperture 25, and which is structured to engage the eye disposed therein, also in a fluid impervious manner. It will therefore be appreciated that upon the positioning segment 20 being disposed in engaging relation with the eye, that an effective, generally air-tight seal can be achieved about the eyeball and a vacuum chamber 22 between retention plate 23 and flange member 24. Additionally, as illustrated in FIG. 2, a channel 29 may also be defined in the vacuum chamber 22, the channel 29 enhancing the effectiveness of a vacuum applied, either alone or in combination with a rigid or flexible insert as provided in U.S. Pat. No. 5,772,675.

Looking further to the flange member 24, as it defines the outer perimeter for engagement with the eye, in the illustrated embodiment, the flange member 24 is disposed in more closely spaced relation to a perimeter of the aperture 25 than is the case in conventional positioning assemblies. Although this closer spacing may be defined only at a latitudinal radius of the aperture 25 in response to the reduced dimension of the narrowed ocular access, it is generally preferred that the flange member 24 define a circular configuration which is uniformly spaced from the aperture 25 and facilitates proper centration of the eye. In the illustrated embodiment, the latitudinal diameter of the flange member 24, generally at the lower edge 27 which engages the eye, is generally between about 0.675 and 0.725 inches. More precisely, a latitudinal diameter of less than generally about 0.79 inches, or 0.708 inches (18 mm) is preferred to correspond an aperture 25 diameter of generally between about 0.350 to 0.475 inches, or more precisely, 0.420 inches in order to form an 8.5 mm flap. For example, the present invention, with the closely space flange member 24 can be utilized to form a 7.5 mm, 8.5 mm, 9.5 mm, or other dimension incision merely by modifying a size of the aperture to the corresponding 0.375 inch, 0.420 inch and 0.465 inch diameters. As can be appreciated, however, reducing a diameter of the flange member 24, while retaining a necessary sized opening, reduces the depth to which the positioning assembly 10 can pass down onto the eye. Still, however, it is desirable to maintain the same diameter of the eye exposed through the cornea, and through preferably a standard dimension aperture 25 so as to generate the appropriately sized corneal flap. As such, the present invention also preferably includes a reduced depth of the positioning segment 20, as defined by the flange member 24. In the illustrated embodiment, the depth of the positioning segment 20, as generally defined from an upper surface of the retention plate 23 to the lower edge 27 of the flange member 24, is preferably less than generally about 0.175 inches and more preferably between about 0.1 to 0.15 inches. In the illustrated embodiment wherein a preferred 0.420 inch diameter aperture 25 and 0.708 diameter flange member are utilized, the preferred depth is 0.115 inches. As a result of the preceding, however, a sufficient portion of the eye is exposed through the aperture 25, and restrictions in access to the eye based upon the physical characteristics of the patient are obviated, with the positioning segment 20 fully and securely engaging the surface of the eye.

The positioning assembly of the present invention is further directed for use with and may at least partially comprise a suctioning assembly 30 for at least temporarily attaching the positioning segment 20 to the eye on which surgery is to be performed once it has been properly positioned thereon. Preferably, the suctioning assembly 30 comprises a vacuum port 32 formed in the positioning segment 20 and a vacuum assembly (not shown) for providing a suction force. The vacuum assembly is structured to apply a suction force which is sufficient to attach the positioning segment 20 to the eyeball about the cornea, C, and cause the cornea to be urged upwardly and to protrude through the aperture 25 of the positioning segment 20, while not being so strong as to cause damage to the eyeball. It will be appreciated from the drawings that the vacuum port 32 formed in the positioning segment 20 is operably coupled to and in fluid flow communication with the vacuum assembly such that the suction force is applied therethrough. Specifically, a preferably removable, externally threaded vacuum handle (not shown), which may also provide a convenient means of grasping and manipulating the positioning assembly 10, is preferably screwed into the vacuum port 32 in a secure, fluid impervious manner. Indeed, such an internally threaded configuration of at least a portion of the vacuum port 32 ensures a more secure engagement and significantly facilitates cleaning of the positioning assembly 10 as the vacuum handle can be secured to ensure no gap, which could potentially become clogged, is present therebetween, and easy access to the interior of the vacuum port 32 can be achieved for cleaning. Moreover, in the preferred embodiment, the vacuum port 32 extends to an undersurface 28 of positioning segment 20 either through retention plate 23 or flange member 24 and into the vacuum chamber 22. Thus, the vacuum port 32 is disposed to provide a suction force, once the vacuum assembly is activated, to a point radially exterior of the aperture 25 and radially interior of the flange member 24, so as to form a seal about the cornea of the eye about to undergo surgery. It should be clear at this point that the structure of positioning segment 20, when accompanied by a suction force, acts to properly position and align the cornea C, for surgery and to generally maintain that position during surgery. Typically, a vacuum of about 25 inches of Hg at sea level will be used.

The positioning assembly 10 of the present invention also preferably includes a guide track 40 formed thereon. The guide track 40 is preferably formed directly on and integrally with the positioning segment 20 so as to guide and facilitate movement of the microkeratome cutting head assembly 15 during the surgical cutting of the cornea. The integral machining is preferred in the illustrated, more compact embodiment, as it ensures that a secure and stable connection between the guide track 40 and the positioning segment 20 is maintained at all times, and ensures that no mis-alignment therebetween will occur as a result of assembly and manufacturing. In particular, some positioning assemblies include a separately machined guide track secured to the positioning segment 20 by one, but typically two or more screws. Two or more screws were generally preferred because the use of one screw might lead to improper alignment of the guide track relative to the aperture if extreme care and precision is not maintained during manufacture and assembly. Based upon the more compact design of the illustrated embodiment, however, it is generally impractical to include multiple screws. Accordingly, in the illustrated more compact embodiment, as well as in other embodiments, in order to maintain precision and ease of assembly, the guide track 40 is preferably integrally formed, such as by machining to a width of about 0.03 inches, with the positioning segment. Also, referring to FIGS. 1 and 2, in the preferred embodiment, the guide track 40 extends along a length of at least one side of positioning segment 20, but preferably extends latitudinally beyond the positioning segment 20 so that engagement between the cutting head assembly and the guide track occurs at a point before the aperture. The present invention recognizes that although a limited dimension must be employed for the outermost engagement by the flange member 24 with the eye, a relatively elevated guide track 40 need not be constrained to the same extent. The guide track 40 of the present invention is configured to extend beyond the retention plate 23 so as to further guide and/or stabilize the microkeratome cutting head assembly 15 before and during a cut across the aperture 25, thereby ensuring complete formation of the corneal flap desired in most cases, and at a starting point before the edge of the aperture 25. It will also be appreciated from the drawings that the guide track 40 includes a toothed upper surface 42 and a retaining lip 44, and extends across the positioning segment in a generally arcuate or semi-circular path. The guide track thereby retains and/or pins the cutting head assembly 15 operatively and downwardly engaged on the eye, and may at least partially guide the movement of the cutting head assembly 15, along the arcuate cutting path best illustrated in FIGS. 9A–9C with regard to a left eye, such as through the engagement of a gear structure of the cutting head assembly 15 on the toothed upper surface 42 of the guide track 400.

Looking once again to the vacuum port 32 of the suctioning assembly 30, as illustrated in the Figures, it is preferably angled outwardly away from a vertical axis of the aperture 25 and/or outwardly away from the guide track 40. As a result, when a hose or other conduit is coupled thereto for supplying the suction force, neither the vacuum port or the conduit will obstruct or otherwise interfere with the movement of the cutting head assembly 15 at least partially over the guide track 40. Furthermore, in the illustrated embodiment, such a configuration permits the more compact, preferably circular configuration of the positioning segment 20 to be maintained, while still effectively directing the suction force to the vacuum chamber 22. Moreover, the integral formation of the guide track 40 with the positioning segment, and generally the vacuum port 32, further contributes to the more compact configuration, as a space for screws and/or other fasteners need not be provided. It is also noted that the vacuum port 32 itself preferably does not extend above a plane of the guide track 40, also contributing to the streamlined nature of the present positioning assembly 10.

Also in the illustrated embodiment, the present invention also preferably includes a pivot assembly. The pivot assembly is structured to provide increased stability to the cutting head assembly 15 during its movement along the arcuate path, and also preferably to define a pivot axis which can stabilize or alternately further guide the movement of the cutting head assembly 15 in conjunction with the guide track 40. The pivot assembly preferably includes a post member 50. The post member 50 is preferably a rigid upstanding element disposed generally opposite the guide track 40. As will again be appreciated from the drawings, in the preferred embodiment, wherein positioning assembly 10 has a teardrop shape, a base section 55, also preferably part of the pivot assembly, is integrally formed with and extends from the positioning segment 20. The base section 55 provides a support surface at which the preferably separately formed post member 50 is secured, as will be described subsequently, during assembly. Moreover, from the explanation which follows, it will become clear that guide track 40 and post member 50 permit the cutting head assembly 15 of the invention, in a preferred embodiment, to become effectively guided and securely received on the positioning assembly 10 in two places, while still permitting the cutting head assembly 15 to be smoothly and slidably moved over the positioning segment 20 along a generally arcuate path, by way of a pivoting motion about the pivot axis defined by the post member 50. Of course, the positioning assembly 10 could also be formed to include another guide track, which extends along a length of the other side of positioning segment 20, also preferably, on an upper surface thereof, so as to also permit the cutting head assembly 15 of the invention to become effectively guided and securely received on the positioning segment 20 in two places while still permitting the cutting head assembly 15 to be smoothly and slidably moved over positioning segment 20 along a generally arcuate path. As a result, either the pivot assembly and/or one or more guide tracks function to direct the arcuate movement of the cutting head assembly 15.

Figure 3:
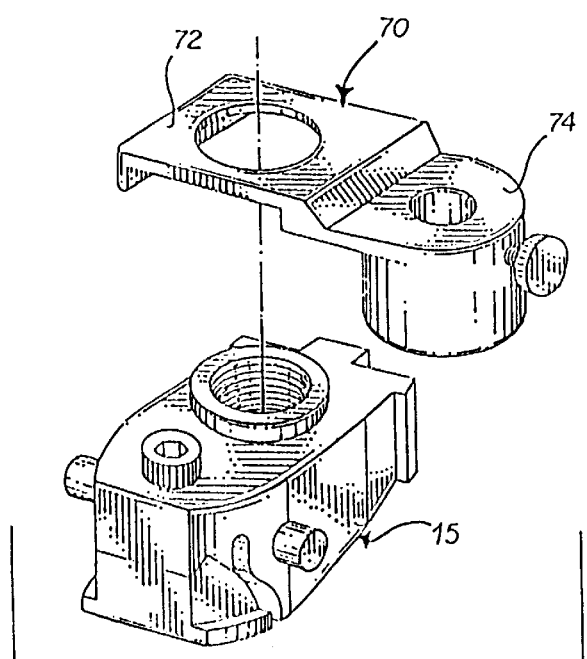
FIG. 3 is an exploded perspective view of the coupling assembly of the positioning assembly, and an associated microkeratome cutting head assembly.

Also preferably included as part of the pivot assembly is a coupling member 70. While the cutting head assembly 15 might be directly and yet movably engaged with the positioning segment 20 for performing an operation on the eye, preferably, the coupling member 70 is utilized as part of the invention, which is structured and disposed to movably and operably couple the cutting head assembly 15 to the positioning segment 20, preferably via the post member 50, while simultaneously permitting movement of the cutting head assembly 15 relative to positioning segment 20. As illustrated in FIG. 3, the coupling member 70 preferably comprises two segments: a) a retaining segment 72 and b) a pivot segment 74. The retaining segment 72 is preferably structured and disposed to be fitted onto a top surface of the cutting head assembly 15 so as to be effectively and removably secured thereto, and move in association with the movement of the cutting head assembly 15. Turning to the pivot segment 74 of coupling member 70, it is structured and disposed to be coupled to the post member 50 and to permit coupling member 70, and accordingly, the cutting head assembly 15 connected thereto, to pivotally move about the pivot axis. Preferably, the pivot segment 74 includes a bushing having a bore 75 formed therein, which is sized to receive a substantial height of the post member 50, thereby captivating it therein.

Figure 8:
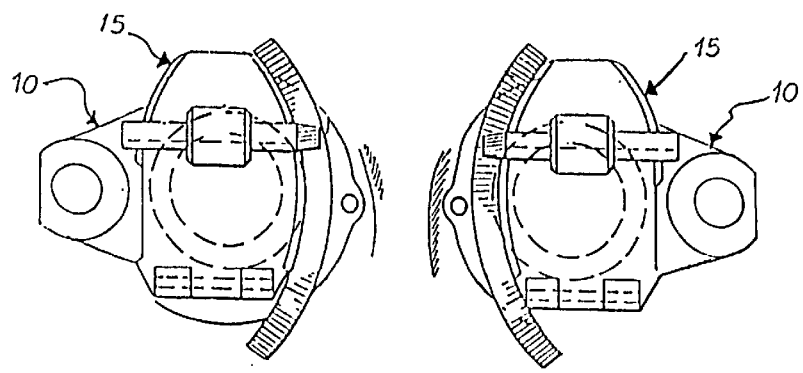
FIG. 8 is an illustration of a microkeratome assembly incorporating the positioning assembly of the present invention appropriately disposed on a corresponding eyes of a patient.

Looking once again to the pivot assembly, and preferably the post member 50 thereof, it preferably defines a cut origination control. The cut origination control is structured to define at least one origination point, as in FIG. 9A, at which operative pivotal movement of the coupling member 70, and accordingly the cutting head assembly 15, about the pivot axis commences. In particular, the cut origination control is configured to substantially ensure that the cutting head assembly 15 cannot engage the eye and/or the guide track 40, such that an incision can be formed, unless it is properly disposed an appropriate origination point. Additionally, the cut origination control ensures that the cutting head assembly 15 is not positioned so as to begin to cut the retention plate 23, eye lid and/or other instruments and articles disposed peripherally to the aperture 25 and the eye. In the illustrated embodiment, the cut origination control includes at least one, but preferably a pair of slots 51, 52 defined in the post member 50. The slots 51, 52, which are preferably, but not necessarily, generally vertically oriented, each define an origination point, such as for the left and right eye, and in the illustrated embodiment are disposed at an angular separation of approximately 100 degrees from center line to center line. In particular, as the positioning assembly 10 of the present invention is structured preferably for use on either eye, as illustrated in FIG. 8, a different origination point on opposite sides of the positioning segment 20 must be defined depending upon the direction of travel. In either instance, however, each of the slots 51, 52 is structured to at least partially receive a restrictor element 78 defined preferably in the bore 75 of the coupling member 70. Specifically, the restrictor element 78 is structured and disposed to fit within a corresponding slot 51, 52, but to restrict passage of the coupling member 70 onto the post member 50 if they are not properly aligned. Along these lines, it is noted that multiple and/or more elaborate configurations could be equivalently utilized so as to provide the restriction if the members are not aligned. Furthermore, although inadvertent passage of the restrictor element 78 into the incorrect slot 51, 52 could result, the necessary positioning of said slots 51, 52 is such that the cutting head assembly 15 would be disposed with its blade beyond the aperture 25 such that an improper cut could still not result.

Because the orientation of the slots 51, 52 relative to the positioning segment 20 generally defines the location of the origination point, it is necessary to ensure that the post member 50 be secured to the base section 55 in a precisely aligned manner. Although a multiple screw configuration could be utilized to provide a certain degree of precision alignment, in the illustrated embodiment, the post member 50 includes an alignment segment 57 structured to operatively engage the base section 55 so as to ensure properly axially aligned securement of the post member 50 thereto. In particular, the base section 55 includes an alignment edge 56 which is matingly engaged by the alignment segment 57 of the post member 50. In the illustrated embodiment, a surface 57' of the alignment segment 57 and alignment edge 56 are straight surfaces which can be confrontingly engaged to provide the aligned securement, however, other mating configurations could also be employed. Based upon the preceding structure, however, proper, precise aligned securement of the post member 50 on the base section 55 can be achieved, such as through the passage of a fastener element through an opening 55' in the base section 55 and into the post member 50.

As a result, based upon the preceding, the cutting head assembly 15 cannot engage the eye unless it is at the appropriate starting point. Furthermore, however, so as to permit the requisite pivotal movement between the post member 50 and the coupling member 70, a channel 58 is preferably formed in the post member 50 so as to permit sliding passage of the restrictor element 78 therethrough during pivotal movement of the coupling member 70, and accordingly the cutting head assembly 15 relative to the post member 50. It is of course understood that the restrictor element 78 could be equivalently disposed on the post member, with the slot(s) defined in the coupling member. In either configuration, however, the channel 58 also functions to ensure that the coupling member 70 does not pivot relative to the post member 50, but rather that it is pinned down into a uniform plane of motion in much the same manner that the retaining lip 44 pins down the cutting head assembly 15 at the guide track 40.

Since many modifications, variations and changes in detail can be made to the described preferred embodiment of the invention, it is intended that all matters in the foregoing description and shown in the accompanying drawings be interpreted in the illustrative and not in a limiting sense. Thus, the scope of the invention should be determined by the appended claims and their legal equivalents.

Now that the invention has been described,
What is claimed is:

1. For retaining, positioning and at least partially exposing during a surgical procedure, a cornea of an eye that is disposed in a latitudinally narrowed ocular access, a positioning assembly comprising:
  a) a positioning segment, said positioning segment including a retention plate;
  b) said retention plate including an aperture defined therein and structured to receive and expose the cornea of the eye therein;
  c) said positioning segment further including a flange member disposed about said aperture and structured to engage the eye;
  d) said flange member being disposed a closely spaced apart distance from said aperture at least at a latitudinal radius thereof;
  e) a pivot assembly structured to define a pivot axis for a cutting head assembly's movement across the aperture; said pivot assembly comprising at least a post member to generally define said pivot axis;
  f) a coupling member pivotally interconnecting said pivot assembly and said cutting head assembly;
  g) said pivot assembly further comprising a cut origination control structured to define an origination point for operative pivotal movement of said coupling member, and accordingly the cutting assembly; and
  h) said cut origination control comprising a slot defined in said post member, said coupling member including a restrictor element structured to restrict operative engagement of said coupling member with said post member unless correspondingly disposed in said slot.

2. For retaining, positioning and at least partially exposing a cornea of an eye during a surgical procedure, a positioning assembly comprising:
  a) a positioning segment, said positioning segment including a retention plate;
  b) said retention plate including an aperture defined therein and structured to receive and expose the cornea of the eye therein;
  c) a pivot assembly structured to define a pivot axis for a cutting head assembly which moves arcuately across the aperture;
  d) said pivot assembly including at least a post member to generally define said pivot axis;

e) a coupling member, said coupling member pivotally interconnecting said post member and said cutting head assembly;

f) said pivot assembly further comprising a cut origination control structured to define an origination point for operative pivotal movement of said coupling member, and accordingly the cutting head assembly; and g) said cut origination control comprising a slot defined in said post member, said coupling member including a restrictor element structured to restrict operative engagement of said coupling member with said post member unless correspondingly disposed in said slot.

3. For retaining, positioning and at least partially exposing a cornea of an eye during a surgical procedure, a positioning assembly comprising:

a) a positioning segment, said positioning segment including a retention plate;

b) said retention plate including an aperture defined therein and structured to receive and expose the cornea of the eye therein;

c) a post member structured to at least partially define a pivot axis for a cutting head assembly which moves arcuately across said aperture;

d) a base section, said post member operatively extending from said base section;

e) said post member including an alignment segment structured to operatively engage said base section so as to ensure properly axially aligned securement of said post member thereto; and f) said base section including an alignment edge, said alignment segment of said post member structured to matingly engage said alignment edge.

* * * * *